United States Patent [19]

Anderson et al.

[11] Patent Number: 5,155,135

[45] Date of Patent: Oct. 13, 1992

[54] BENZAMIDE COMPOUNDS, THEIR PREPARATION AND THEIR USE AS PESTICIDES

[75] Inventors: Martin Anderson, Whitestable; Antony G. Brinnand, Faversham, both of England; Pieter A. Verbrugge, Amsterdam, Netherlands

[73] Assignee: Shell Internationale Research Maatschappij, B.V., Netherlands

[21] Appl. No.: 446,606

[22] Filed: Dec. 6, 1989

[30] Foreign Application Priority Data

Dec. 21, 1988 [GB] United Kingdom ............... 8829817

[51] Int. Cl.$^5$ ............... C07C 335/38; C07C 275/62; A01N 47/34; C07D 213/643

[52] U.S. Cl. .......................... 514/591; 71/94; 71/99; 71/105; 71/120; 514/344; 514/348; 514/349; 514/522; 514/524; 514/584; 546/288; 546/296; 546/297; 558/415; 564/23; 564/38

[58] Field of Search ............... 564/23, 44, 38; 514/584, 591, 349, 522; 558/415; 546/297

[56] References Cited

U.S. PATENT DOCUMENTS 3,748,356  7/1973  Wellinga et al. ............... 564/44

FOREIGN PATENT DOCUMENTS

| | | |
|---|---|---|
| 161019 | 11/1875 | European Pat. Off. . |
| 52833 | 6/1982 | European Pat. Off. . |
| 0107214 | 5/1984 | European Pat. Off. . |
| 0161019 | 11/1985 | European Pat. Off. . |
| 176868 | 4/1986 | European Pat. Off. . |
| 193249 | 9/1986 | European Pat. Off. . |
| 3217619 | 11/1983 | Fed. Rep. of Germany . |
| 7105350 | 10/1972 | Netherlands . |
| 1324293 | 7/1973 | United Kingdom . |
| 1460419 | 1/1977 | United Kingdom . |
| 86/03941 | 7/1986 | World Int. Prop. O. . |

OTHER PUBLICATIONS

Bordas et al., Abstr. Pap. Am. Chem. Soc. (192 Meet., AGRO 40, 1986).

*Primary Examiner*—Richard L. Raymond
*Assistant Examiner*—Peter G. O'Sullivan

[57] ABSTRACT

This invention provides benzamide compounds of general formula

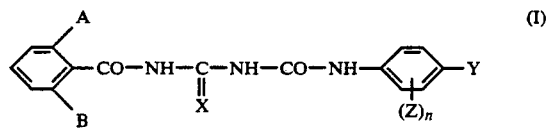

wherein each of A and B independently represents a hydrogen or halogen atom, X represents an oxygen or a sulphur atom, n is 0, 1, 2, 3 or 4, each Z moiety independently represents a halogen atom or a $C_{1-6}$ alkyl group, and Y represents a $C_{1-6}$ haloalkyl group, a $C_{1-6}$ haloalkoxy group, a group of formula

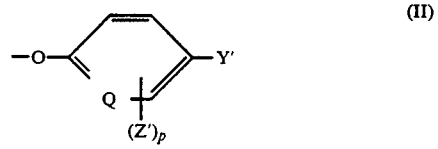

wherein P is 0, 1 or 2, each Z' moiety independently represents a halogen atom or a $C_{1-6}$ alkyl group, Y' represents a $C_{1-6}$ haloalkyl, $C_{1-6}$ haloalkoxy, nitro or cyano group and Q represents N or C-H, or, when n is 2 or 3, Y may also be a halogen atom; processes for their preparation; and their use as pesticides.

22 Claims, No Drawings

BENZAMIDE COMPOUNDS, THEIR PREPARATION AND THEIR USE AS PESTICIDES

This invention relates to benzamide compounds, to processes for their preparation, and to their use as pesticides.

EP-A-193 249 (Duphar) discloses a class of 1,3-substituted urea compounds of formula $R_1$-Z-$R_2$, having anti-tumour activity. One group of compounds within this class has the general formula

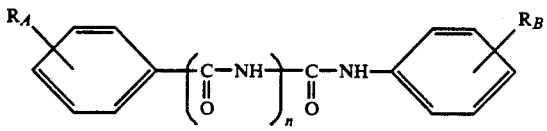

wherein n is 1 or 2. Numerous compounds are disclosed wherein n is 1. However only one compound is mentioned (Page 11, Table A, Comp. No. 16) wherein n is 2, viz. the compound wherein n is 2, $R_A$ is 2-chloro-6-hydroxy, and $R_B$ is 4-chloro. The compounds of formula $R_1$-Z-$R_2$ wherein Z has the formula

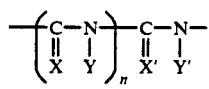

where X is an oxygen atom, Y is a hydrogen atom and n is 2 are described as being obtainable by reacting a compound of formula

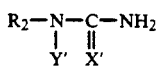

with a compound of formula

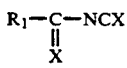

preferably in the presence of an organic solvent, for example an aromatic hydrocarbon, an alkyl halide, a non-cyclic or cyclic dialkyl ether, or acetonitrile, at temperature between 0° C. and the boiling point of the solvent used.

The published abstract of a paper entitled "Some new insect molt inhibitors derived from benzoylbiurets" by Bordas et al., Abstr. Pap. Am. Chem. Soc. (192 Meet., AGRO 40, 1986) states that a series of benzoyl biurets of formula

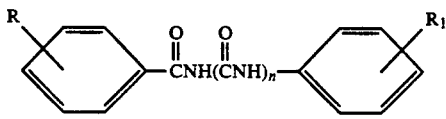

wherein n is 2 were made and that some were larvicidal. However the only meanings given in respect of R and $R_1$ are for the single compound wherein R is 2,6-difluoro, n is 2 and $R_1$ is 4-chloro.

There has now been discovered a class of benzoyl compounds which exhibit a surprising level of pesticidal activity.

According to the present invention therefore there are provided benzamide compounds of general formula

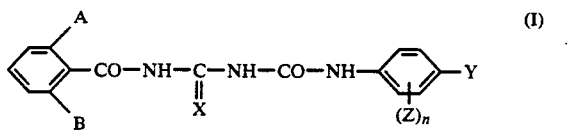

wherein each of A and B independently represents a hydrogen or halogen atom, X represents an oxygen or a sulphur atom, n is 0, 1, 2, 3 or 4, each Z moiety independently represents a halogen atom or a $C_{1-6}$ alkyl group, and Y represents a $C_{1-6}$ haloalkyl group, a $C_{1-6}$ haloalkoxy group, a group of formula

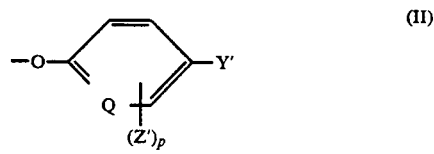

wherein p is 0, 1 or 2, each Z' moiety independently represents a halogen atom or a $C_{1-6}$ alkyl group, Y' represents a $C_{1-6}$ haloalkyl, $C_{1-6}$ haloalkoxy, nitro or cyano group and Q represents N or C—H, or, when n is 2 or 3, Y may also be a halogen atom.

Except where otherwise stated herein, any alkyl group preferably has up to 4 carbon atoms, and is more preferably methyl. Halogen atoms may generally be fluorine, chlorine, bromine or iodine atoms, with fluorine and chlorine being preferred. Preferred haloalkyl and haloalkoxy groups include trifluoromethyl and trifluoromethoxy groups.

Preferred compounds of formula I have one or more of the following features:

(i) each of A and B independently represents a hydrogen, fluorine or chlorine atom, (ii) A and B are both fluorine atoms and X represents an oxygen atom, (iii) each Z moiety independently represents a fluorine or chlorine atom or a methyl group, (iv) each Z moiety independently represents a fluorine or chlorine atom, (v) Y represents a trifluoromethyl group, a trifluoromethoxy group, a group of formula II wherein Z' represents a chlorine atom and p is 1, or, when n is 2 or 3, Y may also be a fluorine or chlorine atom, (vi) n is 0, 1, 2 or 3, (vii) Y represents a trifluoromethyl group, a group of formula II wherein $(Z')_p$ represents a chlorine atom in the position ortho to the oxygen linkage and Y' represents a trifluoromethyl, nitro or cyano group, or, when n is 3, Y may also be a fluorine or chlorine atom, (viii) $(Z)_n$ represents 1, 2 or 3 substituents selected from a fluorine atom attached at the 2-position relative to the point of attachment of the —NH— linkage and chlorine atoms attached at the 3- and 5-positions relative to the point of attachment of the —NH— linkage, (ix) Y represents a 2-chloro-4-(trifluoromethyl) phenoxy group, a 2-chloro-4-nitrophenoxy group, a 2-chloro-4-cyanophenoxy group or a fluorine atom.

Preferred combinations of the above features include (i) or (ii), (iii) and (v); (i) or (ii), (iv), (vi) and (vii); (i) or (ii), (vii) and (viii); (i) or (ii), (viii) and (ix).

Further in accordance with the invention there is provided a process for the preparation of a compound of general formula I as defined above which comprises reacting a compound of formula

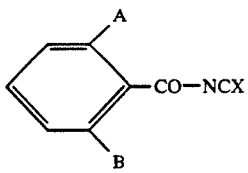

(III)

wherein A, B and X are as defined above, with a compound of general formula

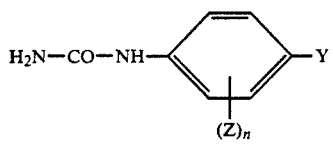

(IV)

wherein n, Z and Y are as defined above.

The reaction is suitably carried out in the presence of an inert solvent. Suitable solvents are aromatic solvents such as benzene, toluene, xylene, or chlorobenzene, hydrocarbons such as petroleum fractions, chlorinated hydrocarbons such as chloroform, methylene chloride or dichloroethane, ethers such as diethyl ether, dibutyl ether, dioxan or tetrahydrofuran, and ketones, such as acetone and methylethylketone. Mixtures of solvents are also suitable. The preferred solvent is toluene.

The reaction may conveniently be effected at temperatures in the range from 0° C. to the reflux temperature of the reaction mixture, e.g. ambient temperature to the reflux temperature. Preferably the molar ratio of compound of formula III to compound of formula IV is from 1:1 to 2:1. Preferably the reaction is carried out under anhydrous conditions.

The compounds of formula III may be prepared as described in UK Patent Specification No. 1,324,293, or by methods analogous thereto.

Certain of the compounds of formula IV are novel and themselves form an aspect of the present invention. The invention thus provides compounds of formula IV having features (iv), (vi) and (vii); (vii) and (viii); and (viii) and (ix) above.

The compounds of formula IV may be prepared by reaction of an aniline of formula

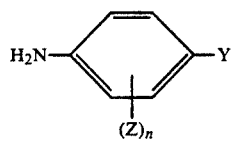

(VII)

wherein n, Z and Y are as defined above, with phosgene, (e.g. at a temperature in the range from ambient temperature to reflux temperature) in an inert solvent (e.g. one of those listed above for reaction of the compounds of formulae III and IV), followed by reaction of the resulting compound with ammonia (e.g. at ambient temperature and in the same inert solvent).

The compounds of formula VII are either known, see for example UK Patent Specification No. 1,460,419, EP-A-161 019, EP-A-52 833, and EP-A-176 868, or may be prepared by methods analogous thereto.

The novel compounds of formula IV also have utility, in accordance with the present invention, in the preparation of a compound of formula

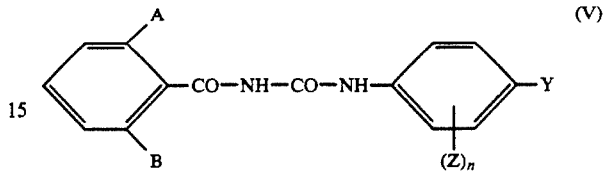

(V)

wherein A and B are as defined above, n is 0, 1, 2 or 3, Z is as defined in features (iii), (iv) or (viii) above and Y is as defined in feature (v), (vii) or (ix) above, by a process which comprises reacting the compound of formula IV with a compound of formula

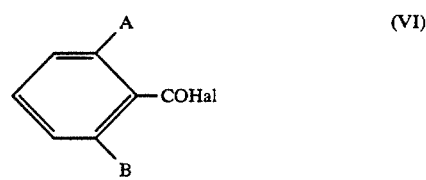

(VI)

wherein Hal is a halogen atom, preferably a chlorine atom.

Compounds of formula VI are known compounds or may be prepared by analogous methods to those known for the preparation of known compounds of formula VI.

Compounds of general formula I exhibit pesticidal, particularly insecticidal and/or acaricidal, activity. Accordingly the invention also provides a pesticidal composition comprising a compound of general formula I in association with at least one inert carrier therefor. The invention further provides a method of combating pests at a locus, which comprises applying to the locus a pesticidal compound or composition according to the invention.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating pesticidal compositions may be used. Preferably compositions according to the invention contain 0.5 to 95% by weight of active ingredient.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montomorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes; and solid-fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example kerosine and light mineral oils; chlorinated hydrocarbons, for example carbon tetrachloride, perchloroethylene and trichloroethane. Mixtures of different liquids are often suitable.

Agricultural compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 or 75% w of active ingredient and usually contain in addition to solid inert carrier, 3–10% w of a dispersing agent and, where necessary, 0–10% w of stabiliser(s) and/or other additives such as penetrants or stickers. Dusts are usually formulated as a dust concentrate having a similar composition to that of a wettable powder but without a dispersant, and are diluted in the field with further solid carrier to give a composition usually containing ½–10% w of active ingredient. Granules are usually prepared to have a size between 10 and 100 BS mesh (1.676–0.152 mm), and may be manufactured by agglomeration or impregnation techniques. Generally, granules will contain ½–75% w active ingredient and 0–10% w of additives such as stabilisers, surfactants, slow release modifiers and binding agents. The so-called "dry flowable powders" consist of relatively small granules having a relatively high concentration of active ingredient. Emulsifiable concentrates usually contain, in addition to a solvent and, when necessary, co-solvent, 10–50% w/v active ingredient, 2–20% w/v emulsifiers and 0–20% w/v of other additives such as stabilisers, penetrants and corrosion inhibitors. Suspension concentrates are usually compounded so as to obtain a stable, non-sedimenting flowable product and usually contain 10–75% w active ingredient, 0.5–15% w of dispersing agents, 0.1–10% w of suspending agents such as protective colloids and thixotropic agents, 0–10% w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as antifreeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick 'mayonnaise'-like consistency.

The composition of the invention may also contain other ingredients, for example other compounds possessing pesticidal, herbicidal, or fungicidal properties. The compounds of the invention are especially useful when applied in admixture with other insecticides, especially organophosphates and pyrethroids. Mixtures with the commercial products fenvalerate, permethrin, cypermethrin, deltamethrin and alphamethrin are especially useful.

The invention will be further understood from the following illustrative examples, in which Example 1 relates to the preparation of an intermediate of formula IV, Examples 2 to 14 relate to the preparation of compounds of formula I, and Examples 15 and 16 relate to pesticidal activity tests.

EXAMPLE 1

Preparation of N-(4-(2-chloro-4-(trifluoromethyl) phenoxy)-2-fluorophenyl)urea

A solution of 4-(2-chloro-4-(trifluoromethyl) phenoxy)-2-fluoroaniline (3.1 g) in dry toluene (25 ml) was added over 15 minutes to a stirred saturated solution of phosgene in toluene (200 ml) whilst the temperature was maintained at 15 to 20° C. with external cooling. The resulting solution was then heated to reflux temperature and kept at that temperature for 1½ hours. The reaction mixture was then allowed to cool to ambient temperature (20° C.), and hydrogen chloride and excess phosgene were purged by passing through the mixture a stream of dry nitrogen. The mixture was then saturated with gaseous ammonia and stirred for 1 hour at ambient temperature (20° C.). The mixture was then evaporated under reduced pressure and the resulting white solid was purified by crystallisation from 9:1 v/v methanol/water to yield N-(4-(2-chloro-4-(trifluoromethyl)phenoxy)-2- fluorophenyl) urea as a colourless crystalline solid (2.3 g, 66%), mp 156–159° C.

EXAMPLE 2

Preparation of N-(((((4-(2-chloro-4-(trifluoromethyl) phenoxy)-2-fluorophenyl)amino)carbonyl)amino) carbonyl)-2,6-difluorobenzamide 2,6-Difluorobenzoyl isocyanate (2.0 g) was added to a solution of N-(4-(2-chloro-4-(trifluoromethyl) phenoxy)-2-fluorophenyl)urea (3.5 g) in dry toluene (80 ml), and the resulting solution was heated at reflux temperature for 4 hours. After cooling to ambient temperature, the reaction mixture was evaporated under reduced pressure and the residue was purified by chromatography over silica using ethyl acetate as eluant to yield N-(((((4-(2-chloro-4-(trifluoromethyl)phenoxy-2-fluorophenyl)amino)-carbonyl)amino)carbonyl)-2,6-difluorobenzamide as a colourless crystalline solid (2.0 g, 38%), mp 191–193° C.

EXAMPLE 2A

Preparation of N-(((((4-(2-chloro-4-(trifluoromethyl) phenoxy)-2-fluorophenyl)amino)carbonyl)amino)-carbonyl)-2,6-difluorobenzamide 2,6-Difluorobenzoyl isocyanate (1.8 g) was added to a solution of N-(4-(2-chloro-4-(trifluoromethyl)phenoxy)-2-fluorophenyl)urea (3.2 g) in dry toluene (50 ml), and the resulting solution was stirred at ambient temperature (20° C.) for 48 hours. The product was then filtered from the reaction mixture, washed with a small amount of 1:2 v/v diethyl ether/light petroleum ether, and dried to yield N-(((((4-(2-chloro-4-(trifluoromethyl)-phenoxy)-2-fluorophenyl)-amino)carbonyl)amino)carbonyl)-2,6-difluorobenzamide as a colourless crystalline solid (4.3 g, 90%), mp 190–192° C.

EXAMPLES 3 TO 14

By similar processes to that of Example 2, except that, instead of reaction at reflux temperature for 4 hours, reaction was for 16–48 hours at ambient temperature (20° C.), there were prepared the following compounds:

3: N-(((((3,5-dichloro-2,4-difluorophenyl)amino)-carbonyl)amino)carbonyl)-2,6-difluorobenzamide (42%), mp 227–229° C.

4: N-(((((4-(3-chloro-5-(trifluoromethyl)pyrid-2-yloxy)-3,5-dichlorophenyl)amino)carbonyl)amino)-carbonyl)-2,6-difluorobenzamide (84%), mp 226–228° C.

5: N-(((((4-(2-chloro-4-(trifluoromethyl)phenoxy)-2-fluorophenyl)amino)carbonyl)amino)thiocarbonyl)-benzamide (23%), mp 172–174.C. (By reaction of benzoyl isothiocyanate with the product compound of Example 1 in acetone for 24 hours at reflux temperature.)

6: N-(((((4-(trifluoromethyl)phenyl)amino) carbonyl)amino)carbonyl)-2,6-difluorobenzamide (93%), mp 230–232° C.

7: N-(((((4-(2-chloro-4-(trifluoromethyl)phenoxy)-phenyl) amino)carbonyl)amino)carbonyl)-2,6-difluorobenzamide (76%), mp 207–208° C.

8: N-(((((4-(2-chloro-4-(trifluoromethyl)phenoxy)-2-fluorophenyl)amino)carbonyl)amino)carbonyl)-6-chlorobenzamide (85%), mp 165–168° C.

9: N-(((((4-(2-chloro-4-(trifluoromethyl)phenoxy)-phenyl)amino)carbonyl)amino)carbonyl)-6-chlorobenzamide (92%), mp 212–215° C.

10: N-(((((4-(trifluoromethoxy)phenyl)amino)carbonyl)amino)carbonyl)-2,6-difluorobenzamide (89%), mp 207–210° C.

11: N-(((((4-(trifluoromethoxy)phenyl)amino)-carbonyl)amino)carbonyl)-6-chlorobenzamide (86%), mp 197–199° C.

12: N-(((((4-(2-chloro-4-(trifluoromethyl)phenoxy)-2-fluorophenyl)amino)carbonyl)amino)carbonyl)-benzamide (93%), mp 220–223° C.

13: N-(((((4-(2-chloro-4-nitrophenoxy)-2-fluorophenyl) amino)carbonyl)amino)carbonyl)-2,6-difluorobenzamide (92%), mp 205–208° C.

14: N-(((((4-(2-chloro-4-cyanophenoxy)-2-fluorophenyl) amino)carbonyl)amino)carbonyl)-2,6-difluorobenzamide (71%), mp 208–210° C.

EXAMPLE 15

Insecticidal Activity

The insecticidal activity of compounds of the invention was assessed, employing Egyptian cotton leafworm larvae, *Spodoptera littoralis* (S.l.), by the following procedure.

Solutions or suspensions of test compound were made up over a range of concentrations in water (initially 0.1%w) containing 10%w acetone and 0.025%w "TRITON X-100" (trade mark) surface active agent (the condensation product of ethylene oxide with an alkyl phenol). These solutions were sprayed at a rate equivalent to 340 litres per hectare ($3.4 \times 10^{-5} m^3/m^2$) onto Petri dishes containing a nutritious diet for Egyptian cotton leafworm larvae. When the spray deposit had dried, each dish was infested with ten 2nd instar larvae.

Mortality assessments were made after 7 days under laboratory conditions (23° C.±2° C., fluctuating humidity and light).

In each test a $LC_{50}$ (the dosage of active material required to kill half of the test species) for the compound was calculated from the mortality L figures and compared with the corresponding $LC_{50}$ for a standard insecticide, ethyl parathion, in the same test. The results are expressed as toxicity indices thus:

$$\text{Toxicity index} = \frac{LC_{50} \text{ (parathion)}}{LC_{50} \text{ (test compound)}} \times 100$$

TABLE I

| Insecticidal Activity | |
|---|---|
| Compound of Example No. | Toxicity Index (S.l.) |
| 2 | 440 |
| 3 | 350 |
| 4 | 110 |
| 5 | 76 |
| 6 | 17 |
| 7 | 250 |
| 8 | 520 |
| 9 | 330 |
| 10 | 18 |
| 11 | 7 |
| 12 | 13 |
| 13 | 77 |
| Comparative A | B |

Grade B denotes that at the initial test concentration (0.1%w) only 40 to 70% mortality was observed. Toxicity indices are only generated for compounds obtaining Grade A (70 to 100% mortality) at the initial test concentration.

Comparative A is the compound N-(((((4-chloro-phenyl) amino)carbonyl)amino)carbonyl)-2,6-difluorobenzamide, disclosed by Bordas et al., Abstr. Pap. Am. Chem. Soc. (192 Meet., AGRO 40, 1986). This compound was also used in Example 16 following.

EXAMPLE 16

Acaricidal Activity

Acaricidal activity of the compounds of Examples 2 and 14 was assessed, employing adult female glasshouse red spider mites, *Tetranychus urticae* (T.u.), by the following procedure.

2 cm diameter leaf discs cut from the leaves of French bean plants were placed, underside uppermost, on 5.5 cm diameter filter papers, kept moist by a cotton wool wick dipped in water.

Each leaf disc was infested with 25 to 30 adult female mites which were removed after 6 hours, leaving about 50 eggs on each disc. Within 5 days the eggs hatched. The freshly emerged larvae on the leaf discs were sprayed with solutions of test compound made up as in Example 15 above, at a rate equivalent to 340 litres per hectare ($3.4 \times 10^5$ m$^3$/m$^2$).

The discs were thereafter kept under normal laboratory conditions (23° C.±2° C., fluctuating humidity and 16 hours day length). After 7 days assessment was made of the number of mites emerging as adults.

From the results the LC$_{50}$ was calculated. For the compound of Example 2 the value was 0.00023%w/v and for the compound of Example 14 the value was 0.0037%w/v. For Comparative A the value was greater than 0.1%w/v.

We claim:

1. A benzamide compound of the formula:

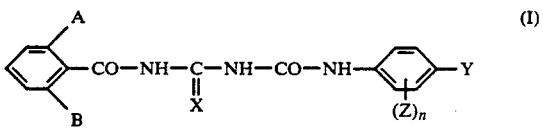

wherein each of A and B independently represents a hydrogen or halogen atom,

X represents an oxygen or a sulphur atom, n is 0, 1, 2, 3 or 4, each Z moiety independently represents a halogen atom or a C$_{1-6}$ alkyl group, and Y represents a C$_{1-6}$ haloalkyl group, a C$_{1-6}$ haloalkoxy group, a group of the formula

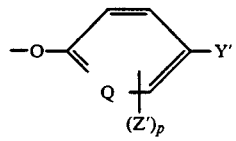

wherein p is 0, 1, or 2, each Z' moeity independently represents a halogen atom or a C$_{1-6}$ alkyl group, Y' representa a C$_{1-6}$ haloalkyl, C$_{1-6}$ haloalkoxy, nitro or cyano group, and Q represents N or C—H, or when n=2 or 3, Y may also be a halogen atom.

2. The compound of claim 1, wherein each of A and B independently represents a hydrogen, fluorine or chlrorine atom, each Z moiety independently represents a fluorine or chlorine atom or a methyl group, and Y represents a trifluoromethyl group, a trifluoromethoxy group, a group of formula II wherein Z' represents a chlorine atom and p is 1 or, when n is 2 or 3, Y may also be a fluorine or chlorine atom.

3. The compound of claim 2, wherein each Z moiety independently represents a fluorine or chlorine atom, n is 0, 1, 2, or 3, and Y represents a trifluoromethyl group, a group of formula II where (Z')$_p$ represents a chlorine atom in the position ortho to the oxygen linkage and Y' represents a trifluoromethyl, nitro or cyano group, or, when n is 3, Y may also be a fluorine or chlorine atom.

4. The compound of claim 3 wherein (Z)$_n$ represents 1, 2 or 3 substituents selected from a fluorine atom attached at the 2-position relative to the point of attachment of the —NH— linkage and chlorine atoms attached at the 3- and 5-positions relative to the point of attachment of the —NH— linkage.

5. The compound according to claim 3 wherein Y represents a 2-chloro-4-(trifluoromethyl)phenoxy group, a 2-chloro-4-nitrophenoxy group, a 2-chloro-4-cyanophenoxy group or a fluorine atom.

6. The compound according to claim 1 wherein A and B are both fluorine atoms and X represents an oxygen atom.

7. The compound according to claim 1, comprising N-(((((4-(2-chloro-4-(trifluoromethyl) phenoxy)-2-fluorophenyl)amino)-carbonyl)amino)carbonyl)-2,6-difluorobenzamide.

8. The compound according to claim 1, comprising N-(((((3,5-dichloro-2,4-difluorophenyl) amino)carbonyl)amino)carbonyl)-2,6-difluorobenzamide.

9. The compound according to claim 1, comprising N-(((((4-(3-chloro-5-(trifluoromethyl) pyrid-2-yloxy)-3,5-dichlorophenyl)-amino) carbonyl)amino)carbonyl)-2,6-difluorobenzamide.

10. The compound according to claim 1, comprising N-(((((4-(2-chloro-4-(trifluoromethyl) phenoxy)-2-fluorophenyl)amino)-carbonyl)amino)thio-carbonyl)-benzamide.

11. The compound according to claim 1, comprising N-(((((4-(trifluoromethyl) phenyl)amino)carbonyl)amino)carbonyl)-2,6-difluorobenzamide.

12. The compound according to claim 1, comprising N-(((((4-(2-chloro-4-(trifluoromethyl) phenoxy)phenyl)amino)carbonyl)-amino)carbonyl)-2,6-difluorobenzamide.

13. The compound according to claim 1, comprising N-(((((4-(2-chloro-4-(trifluoromethyl) phenoxy)-2-fluorophenyl)amino)-carbonyl)amino)carbonyl)-6-chlorobenzamide.

14. The compound according to claim 1, comprising N-(((((4-(2-chloro-4-(trifluoromethyl) phenoxy)phenyl)amino)carbonyl)-amino)carbonyl)-6-chlorobenzamide.

15. The compound according to claim 1, comprising N-(((((4-(trifluoromethoxy) phenyl)amino)carbonyl)amino)carbonyl)-2,6-difluorobenzamide.

16. The compound according to claim 1, comprising N-(((((4-(trifluoromethoxy) phenyl)amino)carbonyl)amino)carbonyl)-6-chlorobenzamide.

17. The compound according to claim 1, comprising N-(((((4-(2-chloro-4-(trifluoromethyl) phenoxy)-2-fluorophenyl)amino)carbonyl)amino)carbonyl)-benzamide.

18. The compound according to claim 1, comprising N-(((((4-(2-chloro-4-(nitrophenoxy) -2-fluoro-phenyl)amino)carbonyl)-amino)carbonyl)-2,6-difluorobenzamide.

19. The compound according to claim 1, comprising N-(((((4-(2-chloro-4-(cyanophenoxy)-2-fluoro-phenyl)amino)carbonyl)-amino)carbonyl)-2,6-difluorobenzamide.

20. A pesticidal composition comprising a pesticidally effective amount of a compound as claimed in claim 1, in association with at least one carrier therefor.

21. A method of combating pests at a locus, which comprises applying to the locus a pesticidally effective amount of a compound as claimed in claim 1.

22. A method of combating pests at a locus, which comprises applying to the locus a pesticidally effective amount of a composition as claimed in claim 20.

* * * * *